US009033939B2

(12) United States Patent
Eberhart et al.

(10) Patent No.: US 9,033,939 B2
(45) Date of Patent: May 19, 2015

(54) NASAL APPLICATOR

(71) Applicant: 5med GmbH, Bad Abbach (DE)

(72) Inventors: Leopold Eberhart, Marburg (DE); Ines Jackl, Marburg (DE); Stefan Nardi-Hiebl, Munich (DE)

(73) Assignee: 5med GmbH, Bad Abbach (DE)

( * ) Notice: Subject to any disclaimer, the term of this patent is extended or adjusted under 35 U.S.C. 154(b) by 0 days.

(21) Appl. No.: 14/025,655

(22) Filed: Sep. 12, 2013

(65) Prior Publication Data

US 2014/0081216 A1 Mar. 20, 2014

(30) Foreign Application Priority Data

Sep. 14, 2012 (DE) .................. 20 2012 008 892 U
Jul. 24, 2013 (DE) .................. 10 2013 012 292

(51) Int. Cl.
*A61M 5/00* (2006.01)
*A61M 11/00* (2006.01)
*A61M 15/08* (2006.01)
*A61M 11/08* (2006.01)

(52) U.S. Cl.
CPC ............. *A61M 11/00* (2013.01); *A61M 11/08* (2013.01); *A61M 15/08* (2013.01); *A61M 2205/3569* (2013.01); *A61M 2205/3592* (2013.01); *A61M 2205/505* (2013.01); *A61M 2205/52* (2013.01); *A61M 2205/6009* (2013.01); *A61M 2205/6018* (2013.01); *A61M 2205/6054* (2013.01); *A61M 2205/609* (2013.01)

(58) Field of Classification Search
CPC . A61M 11/00; A61M 15/08; A61M 2205/52; A61M 2205/609; A61M 2205/505; A61M 11/08; A61M 2205/3569; A61M 2205/6054

USPC ........ 604/65–67, 151, 275, 182, 37, 199, 28, 604/19; 128/200.14–200.23, 203.18, 128/203.22, 207.18
See application file for complete search history.

(56) References Cited

U.S. PATENT DOCUMENTS

| 6,156,008 | A | * | 12/2000 | Castellano | .................... 604/116 |
| 2005/0098583 | A1 | | 5/2005 | Mbonyumuhire | |
| 2005/0245902 | A1 | * | 11/2005 | Cornish et al. | ............. 604/890.1 |
| 2007/0107720 | A1 | * | 5/2007 | Boeck et al. | ............. 128/200.21 |

(Continued)

FOREIGN PATENT DOCUMENTS

| DE | 4021263 A1 | 1/1992 |
| EP | 1293224 A2 | 3/2003 |

(Continued)

*Primary Examiner* — Bhisma Mehta
*Assistant Examiner* — Hamza Darb
(74) *Attorney, Agent, or Firm* — Alleman Hall McCoy Russell & Tuttle LLP

(57) ABSTRACT

A nasal applicator for nasally administering medicinal active pharmaceutical substances and/or ingredients, in particular painkillers or analgetics, includes a dosage device for dosedly discharging the active pharmaceutical substance, dosage determining logic for determining the discharged amount of active pharmaceutical substance as well as a locking device for locking the dosage device, in particular when the determined amount of discharged active pharmaceutical substance reaches a predetermined level. The locking device for locking the discharge dosage device is controlled by an electronic control device with a patient data memory into which an individual patient's control data may be inputted via an input device for individually locking the dosage device for a specific patient.

19 Claims, 3 Drawing Sheets

(56) References Cited

U.S. PATENT DOCUMENTS

| | | | |
|---|---|---|---|
| 2007/0179448 A1* | 8/2007 | Lim et al. | 604/187 |
| 2013/0072755 A1* | 3/2013 | Papania et al. | 600/109 |
| 2013/0276799 A1* | 10/2013 | Davidson et al. | 131/273 |

FOREIGN PATENT DOCUMENTS

| | | |
|---|---|---|
| EP | 2174720 A | 4/2010 |
| EP | 2359938 A1 | 8/2011 |
| EP | 2364785 A1 | 9/2011 |
| EP | 2436415 A1 | 4/2012 |
| FR | 2721521 A1 | 12/1995 |
| GB | 2408214 A | 5/2005 |
| WO | 0141847 A2 | 6/2001 |
| WO | 0141849 A2 | 6/2001 |
| WO | 2007130586 A2 | 11/2007 |
| WO | 2007130639 A2 | 11/2007 |
| WO | 2007130652 A2 | 11/2007 |

\* cited by examiner

NASAL APPLICATOR

CROSS REFERENCE TO RELATED APPLICATIONS

This application claims priority to German Utility Model Application No. 20 2012 008 892.0, entitled "Nasal Applicator," filed Sep. 14, 2012, and also claims priority to German Patent Application No. 10 2013 012 292.9, entitled "Nasal Applicator," filed Jul. 24, 2013, both of which are hereby incorporated by reference in their entirety for all purposes.

TECHNICAL FIELD

The present disclosure relates to a nasal applicator for nasally administering medicinal active pharmaceutical substances and/or ingredients, in particular painkillers or analgetics, including a dosage device for dosedly discharging the active pharmaceutical substance, dosage determining logic for determining the discharged amount of active pharmaceutical substance as well as a locking device for locking the dosage device, in particular when the determined amount of discharged active pharmaceutical substance reaches a predetermined level.

BACKGROUND AND SUMMARY

In pain therapy strong painkillers and/or opioids have to be administered at times, wherein it is advantageous to administer such painkillers via the nasal mucous membrane for reaching a rapid taking effect. Nasal applicators for such purpose are known in a plurality of forms and may be operated in an easy manner by a patient himself. The discharge mandrel of the nasal applicator is inserted into a nostril and then activated so as to discharge a predetermined dose of the painkiller, e.g., in the sprayed form of an aerosol. A discharge dosage mechanism provided in the interior of the nasal applicator may, e.g., include an engine-driven pump, but is at times, however, also a manually operated transport mechanism that may work, e.g., by pressing together the applicator housing or by pushing a delivery piston.

Nasal applicators are, e.g., known from US 2005/0098583, FR 2 721 521 or GB 2 408 214, wherein the latter GB 2 408 214 includes a delivery prevention mechanism for preventing delivery of a substance when the applicator is not properly fitted. Document FR 2 721 521 discloses a nasal applicator for the nasal application of powder.

While on the one hand, self-administration is useful and desired with painkillers so as to administer the painkiller only when it is in fact needed; on the other hand, the patient self-administering the painkiller has to be protected from an unintentional overdose, in particular if highly effective opioid painkillers are concerned.

Therefore, it has previously been suggested to include in such nasal applicators a locking device that locks the dosage device upon reaching a predetermined discharge amount. For example, the company Aptar offers a nasal applicator with a so-called "lockout" system according to which the dosage device is locked and/or rendered inoperable for a predetermined period of time, as soon as a predetermined number of puffs has been discharged and/or a predetermined number of actuations has been reached.

To date, however, such locking devices are ill-suited and/or not efficiently usable for clinical pain therapy with highly effective opioid painkillers, since with such highly effective medicaments the dose is individually determined by a doctor for a specific individual patient so that a predetermined locking of the applicator is too early for one patient and too late for another and/or also leads to use of a second, not yet locked applicator, if any, for which a new active pharmaceutical substance cartridge is to be opened, so as to administer an additional dose.

On the basis thereof it is the objective of the present disclosure to provide an improved nasal applicator of the above-mentioned kind which avoids the disadvantages of the prior art and further develops the latter in an advantageous manner. In particular, a simple and yet safe self-dosing of highly effective painkillers is to be rendered possible which efficiently handles the existing painkiller supplies and still meets an individual patient's needs.

According to the present disclosure, this objective is achieved by a nasal applicator for nasal administration of medicinal active pharmaceutical substances, in particular painkillers, including a dosage device for dosedly discharging the active pharmaceutical substance, dosage determining logic for determining the amount of discharged active pharmaceutical substance as well as a locking device for locking the dosage device when the determined amount of discharged active pharmaceutical substance reaches a predetermined level, characterized in that the locking device is controlled by an electronic control device including a patient data memory into which individual control data of a specific patient can be entered through an input device for individually locking the dosage device for such specific patient. Various alternate embodiments of the present disclosure are laid down in the dependent claims.

The present disclosure suggests to individually control the discharge of active pharmaceutical substance in dependency of a specific patient and to provide therefor an individually programmable control appropriate for a respective user, wherein the relevant control parameters thereof are not yet fixedly preset by the applicator manufacturer but may be entered into the nasal applicator and/or provided for the control thereof in an easy manner by the prescribing doctor and/or his co-workers such as nurses and/or the pharmacist. In accordance with the present disclosure, the locking device for locking the dosage device is controlled by an electronic control device with a patient data memory into which an individual patient's control data may be inputted via an input device for individually locking the dosage device for a specific patient. The locking function of the nasal applicator is thus configurable in dependency of an individual patient, wherein the control device includes a soft, storage programmable logic that may be inputted by the end user and/or the prescribing doctor. Advantageously, the patient data memory is in this connection a repeatedly overwritable, in particular non-volatile read only memory, e.g., in the form of an EPROM, so that the relevant control data such as admissible maximum dose or unlocking code are easily programmable, but remain stored when the apparatus is turned off. Due to the individually adjustable control data the nasal applicator may be configured such that it is suitable for disparate patients, different anamneses and diverging pathologic diagnostic findings, respectively.

In particular, the nasal applicator may be individually configured with regard to the dischargeable maximum amount of active pharmaceutical substance, wherein on the one hand a maximum amount per time, e.g., in the form of microgram/hour, and/or on the other hand also absolute maximum amounts, e.g., with active pharmaceutical substances that are difficult to metabolize, may be predetermined, upon reaching of which maximum amounts the locking device is respectively activated, so that the dosage device may only discharge the respective individually predetermined maximum amount of active pharmaceutical substance. Such admissible active substance maximum amounts may be variably predetermined by inputting the appropriate control data into said patient data memory. In a further development of the present disclosure, the application amounts and/or application maximum amounts that are discharged by the discharge means may for example be controlled in dependency of the patient's weight or his opioid habits.

In this connection, the individual configuration for a specific patient may basically be effected in different ways. In order to achieve an easy inputting of control data into the nasal applicator, the nasal applicator and/or the control device thereof and/or the patient data memory thereof may, in an advantageous further development of the present disclosure, be connected via a data communication interface to a superordinated, external computer, from which all necessary control data for a respective patient and/or user may be inputted. Such external computer may in this connection basically be an off-the-shelf PC onto which a control configuration software adapted to the nasal applicator is installed which software is able to communicate with the control device of the nasal applicator and/or to store the necessary data in the patient data memory thereof. In particular, the nasal applicator may be connected via said data communication interface to a hospital ward computer or a pharmacy or drugstore computer, from which the control functions of the nasal applicator are individually adapted to the intended user, in particular the abovementioned admissible maximum dose, or also other control functions to be adapted individually. Accordingly, the external computer may be an input device to the nasal applicator.

The data interface may basically be adapted in different ways, e.g., in the form of a USB interface, wherein the external computer and/or the control device of the nasal applicator optionally has self-recognition means or self-adaption means, e.g., in the form of an appropriate software module stored in memory of the control device so that upon plugging in of the nasal applicator and/or the connection of the said data communication interface, a self-recognition of the plugged-in apparatus is effected and a configuration according to the plug-and-play principle is possible.

Alternatively or in addition to the configurability via an external data communication interface, the nasal applicator itself may have an appropriate input device rendering it possible to input a patient's individual control data into the control device and/or the patient data memory thereof. The input device at the nasal applicator itself may be advantageously adapted such that it is sufficiently small, e.g., in the form of a keyboard as it is for example known from mobile phones. Advantageously, also a touch screen may be provided as an input device at the nasal applicator, either directly at the housing or in attachable form for example similar to an external PC keyboard connectable to the nasal applicator, if necessary even in wireless manner connectable, wherein in this case the control device of the nasal applicator may contain the necessary functional modules in terms of control technology in order to transform the keyboard entries into appropriate signals. Accordingly, the input device may be a manually operable input device.

In order to simplify the use, the nasal applicator may—for example in the form of the aforesaid touch screen—include a display device for displaying input prompts and already inputted input values by means of which a communication menu and/or a menu control may be provided, which renders it easier for the user to input data and/or directs and instructs him when doing so.

Such an input device at the nasal applicator itself and/or input device attachable thereto may advantageously also be used to keep records of the patient's discomfort. By means of a suitable input element, for example in the form of the aforementioned touch screen, the patient may input discomfort data, which may include one or more of the level of discomfort, the duration of discomfort and/or the frequency of discomfort at the nasal applicator when discomfort occurs. In the easiest case simply the occurrence of a pain pulse may be documented, e.g., by pressing a pain button so that then the frequency of occurrence may be determined and conclusions may be drawn on the basis thereof regarding the applicable dose. Alternatively or in addition in a further development, also the duration of a phase of discomfort may be determined, for example by inputting the beginning and the end, and/or the level of discomfort may be determined, for example by inputting values on a predetermined scale of discomfort level or by pressing the input device several times.

The inputted data regarding level, duration and/or frequency of discomfort may be stored in a storage means directly at the nasal applicator and/or be communicated via a suitable data interface to an external memory so that the stored data may subsequently be evaluated by a doctor or also with the aid of a computer. Alternatively or in addition to such storing of said data, the inputted level, duration and/or frequency of discomfort may also be evaluated by a control module to the effect that a change in the dose and/or the locking of the nasal applicator is aimed at or an adjustment of other functions of the nasal applicator is aimed at by modifying and/or adapting a specific patient's individual control data. For example, dosage algorithms may be adapted, e.g., such that in the case of mixtures of active pharmaceutical substances the mixing ratio is altered and/or the delivered amounts of active substances are altered.

Alternatively or in addition to the aforementioned configuration options, the nasal applicator and/or the control device thereof may also be individually configured for a specific patient by inserting into the nasal applicator at least a part of the control device thereof and/or the patient data memory thereof together with an optionally replaceable active substance cartridge and/or an active substance receptacle the adaption of which is irrelevant. In an advantageous further development of the present disclosure the nasal applicator may include a replaceable active substance receptacle for example in the form of an active substance cartridge or an active substance container, at which active substance receptacle a writable patient data memory may be provided so that for example still in a hospital pharmacy, when providing the pharmaceuticals and/or the active substance for a specific patient, the application stated for example on the prescription, for example including the admissible maximum dose, may be inputted into the patient data memory at the active substance container. For this the aforementioned external memory for example in the form of a hospital ward computer may be equipped with a write/read piece of equipment through which a specific patient's individual control data may be programmed and/or stored in a memory chip fixed to the active substance receptacle. If the active substance receptacle is inserted into the nasal applicator, the chip communicates with the control device and the control data stored in the memory of the chip attached to the receptacle are imported and form the basis for the control of the nasal applicator.

The memory attachable to the active substance receptacle may in this connection basically be adapted in a plurality of forms, for example in the form of a memory chip, if necessary also in other forms such as for example a bar code that is applied to an adhesive label gluable to the active substance receptacle. For example, a code such as a bar code may comprise the input device described herein and may thus store individual control data for a specific patient.

In a further embodiment of the present disclosure, the chip attachable to the active substance receptacle, into which chip a specific patient's individual control data are storable, may also include a part of the control device for the nasal applicator, for example for controlling the locking device thereof, so that not only control data may be read out from the receptacle-sided memory chip, but also control commands may be given by it upon insertion of the active substance receptacle into the nasal applicator.

In the alternative or in addition to such configurability by means of insertion of the active substance receptacle, the nasal applicator and/or the control device thereof may include a wireless signal receiver for receiving a specific patient's individual control data and/or may cooperate with a transmitter that the patient and/or user of the nasal applicator wears on his body or keeps in his direct proximity. By means of such cooperation with such external transmitter the use of the nasal applicator may be significantly improved in particular with regard to safety and misuse, since the necessary control data controlling, in particular unlocking the nasal applicator are available only when or if the "right" patient and/or user is using the nasal applicator.

The aforementioned external transmitter and/or the therewith communicating signal receiver at the nasal applicator may basically be adapted in different ways, wherein advantageously the aforementioned transmitter includes at least part of the aforementioned patient data memory and/or is connected thereto, so that the aforementioned external transmitter has access to the relevant individual control data of a specific patient and may transmit and/or provide these to the control device of the nasal applicator via the signal receiver on the applicator. As an alternative to wireless transmission, in some examples the transmission may be effected by connecting an appropriate signal line.

In a further advantageous embodiment of the present disclosure, the said external transmitter that the patient and/or user may wear on his body may include an RFID element, thus a control element communicating in radio frequency range, in which control element a patient's individual control data are stored which data may be received by an RFID reader and/or sending means at the nasal applicator. Thus, the RFID element constitute the input device in some examples. In the alternative or in addition to such transmission of a patient's individual control data by means of RFID technology, data transmission could, if necessary, also be effected in another suitable format, for example according to the bluetooth standard, wherein, however, use of an RFID element as external data memory wearable on the body is particularly favorable as far as power supply and lack of radiation in its inactive mode are concerned.

The said RFID element may advantageously be fixed directly to the body of the user, for example by means of a wristband or a leg strap, a necklace or another suitable body fastener, but may also be positioned in another manner in proximity of the body, if necessary, for example when used in a hospital by fixing it to the patient's bed.

By means of such external transmitter in particular in the form of the said RFID element, particularly a functional lock and/or an unlocking function may be implemented at the nasal applicator, in particular in such manner that the nasal applicator is only usable and/or operable, if the said transmitter is positioned sufficiently close to the nasal applicator. The basic locking of the nasal applicator and the unlocking in dependency of a specific user's individual code coming along therewith brings about particular advantages, if the locking function also takes into account maximum amounts of the discharged active pharmaceutical substance in the manner described; however, independently thereof it also represents an advantageous embodiment and an independent aspect of the present disclosure.

The nasal applicator and/or the control device thereof may in a further development of the present disclosure be provided with a user identification means such as a user identification device for automatically identifying the user of the nasal applicator and an unlocking device and/or unlocking means such as unlocking logic for unlocking the locking device in dependency of a respective determined user of the nasal applicator. The said user identification device may in this connection basically be adapted in different ways; it may, e.g., include a body feature sensor such as a fingerprint sensor, however, in the alternative or in addition it advantageously has a code receiver for receiving a specific patient's individual code and comparing such received code with a predetermined code. Accordingly, the nasal applicator may be unlocked by inputting and/or importing a code, whereas it may be locked when the correct code is not inputted and/or imported.

In an advantageous further development of the present disclosure, the said individual code of a specific patient may be stored in the aforementioned external memory element in particular in the form of the RFID element, so that the nasal applicator is only unlocked if said RFID element and/or external memory element is kept ready.

In a further development of the present disclosure, the applicator-sided RFID transmitter and/or receiver or—in the alternative or in addition—the RFID element may, in terms of communication range, in particular receiver sensitivity and/or transmitter power, be adapted such that the control data from the RFID element are transmitted only at a distance between the RFID element and the RFID transmitter and/or receiver of less than for a predetermined distance, for example 2 m, and optionally less than 1 m.

In order to be able to easily configure and/or use the nasal applicator for a plurality of active pharmaceutical substances, in particular a plurality of painkillers, the control device of the nasal applicator and/or the storage means thereof may in an advantageous further embodiment of the present disclosure include a plurality of preconfiguration datasets for preconfiguring the control of the locking device and/or the dosage device for a plurality of active pharmaceutical ingredients, from which preconfiguration datasets an appropriate preconfigured dataset is then selectable in dependency of a respective used active pharmaceutical substance. Such selection may be effected via the aforementioned input device, but also, as the case may be, by importing the respective preconfiguration data from the aforementioned external computer, wherein in such case the preconfiguration datasets are provided at the external computer.

In order to simplify the selection of the preconfiguration datasets, the control device of the nasal applicator may include an active pharmaceutical substance identification module which automatically identifies the respective used active pharmaceutical substance and selects the appropriate preconfiguration data. To this purpose an appropriate, importable code may be attached to the active pharmaceutical substance container to be inserted, for example in the chip element fixed to the active substance container or a bar code applied thereto. The active pharmaceutical substance identification module at the nasal applicator includes suitable code detection means such as code detection logic, in order to import and/or detect the code provided at the active pharmaceutical substance container and to select the correct preconfiguration data in dependency of the imported and/or detected code. Such preconfiguration may for example comprise predetermining an absolute maximum amount irrespective of the patient in order to reduce the possible error sources when programming for an individual patient. Alternatively or in addition, said preconfiguration data may include standard control data for a standard administration of the active pharmaceutical substance which may then either be adopted by individually programming for a specific patient or may be altered in the desired way so that only the data in fact deviating from the standard routine are to be inputted.

In order to facilitate self-administration of the active pharmaceutical substance for weaker patients or patients affected by pain therapy they already had, and/or in order to simplify use of the nasal applicator, the nasal applicator may in a further development of the present disclosure include an energy-driven transport actuator which is responsible for or at least supports the transportation and discharging of the active pharmaceutical substance by means of external energy, wherein said transport actuator may work electrically, magnetically, pneumatically or hydraulically or by means of other kinds of energy. In particular, the transport actuator may be provided in the form of a pressure accumulator and/or a spring accumulator, in order to drive a suitable active substance transporting element such as for example a pump or a piston, by means of the stored energy. Accordingly, the user merely has to effect activation of the transport actuator and/or the transport element driven thereby. Hereby, the user is spared from having to press together the nasal applicator and/or from having to push a delivery piston, for example.

If the nasal applicator works in the above described way with a power-driven transport actuator, said locking device may in an easy manner lock the transport actuator and/or render it inactive, for example by interrupting the energy supply or by locking the pressure or spring accumulator. Alternatively or in addition, also a mechanical locking of, for example, the dosage device or the transport element thereof may be provided, for example by engaging a locking latch or similar elements, which also may advantageously be effected by means of external energy.

In advantageous further development of the present disclosure the nasal applicator is provided with a determining and/or detection device which determines and/or detects prior to and/or at the time of discharge of the active pharmaceutical substance whether the nasal applicator is positioned in and/or at the nose, in particular whether the discharge mandrel is positioned inside a nostril, or whether in general the discharged active pharmaceutical substance is in fact applied into the nose. The determining device may basically be adapted in different ways, wherein an advantageous further development may consist in the determining device including a body temperature sensor or generally heat detection means for detecting body heat. If the determining device determines a temperature in the range of body temperature at the nasal applicator, in particular at the discharge mandrel thereof, it may be assumed that the nasal applicator applies the active pharmaceutical substance not just into the environment, but in fact into the nose.

In particular, said determining device may have bi-metal elements at the discharge mandrel and/or infrared elements at or in the region of the discharge mandrel, by means of which positioning of the discharge mandrel at the nose and/or into a nostril may be detected.

The determination of the position of the nasal applicator when discharging the active pharmaceutical substance may be used for a plurality of control functions. In an advantageous further development of the present disclosure the locking device of the nasal applicator may be drivable by said determining device, in particular such that the locking device is only unlocked if the nasal applicator is positioned in and/or at the nose. Hereby it may be avoided that valuable active substance is wasted and/or discharged into the environment.

In the alternative or in addition, data such as a signal from said determining device may be input to the dosage determining logic. In particular, when determining the administered dose, the dosage determining logic may take into account data from the determining device such as whether the nasal applicator is in fact positioned in and/or at a nose at the time of discharge of the active pharmaceutical substance. Discharged active pharmaceutical substance may for example only be considered as administered dose if the determining device determines that the discharge mandrel was correctly positioned inside a nostril.

In the following, the present disclosure is described in more detail on the basis of one exemplary embodiment and related drawings.

DETAILED DESCRIPTION

Figure 1:
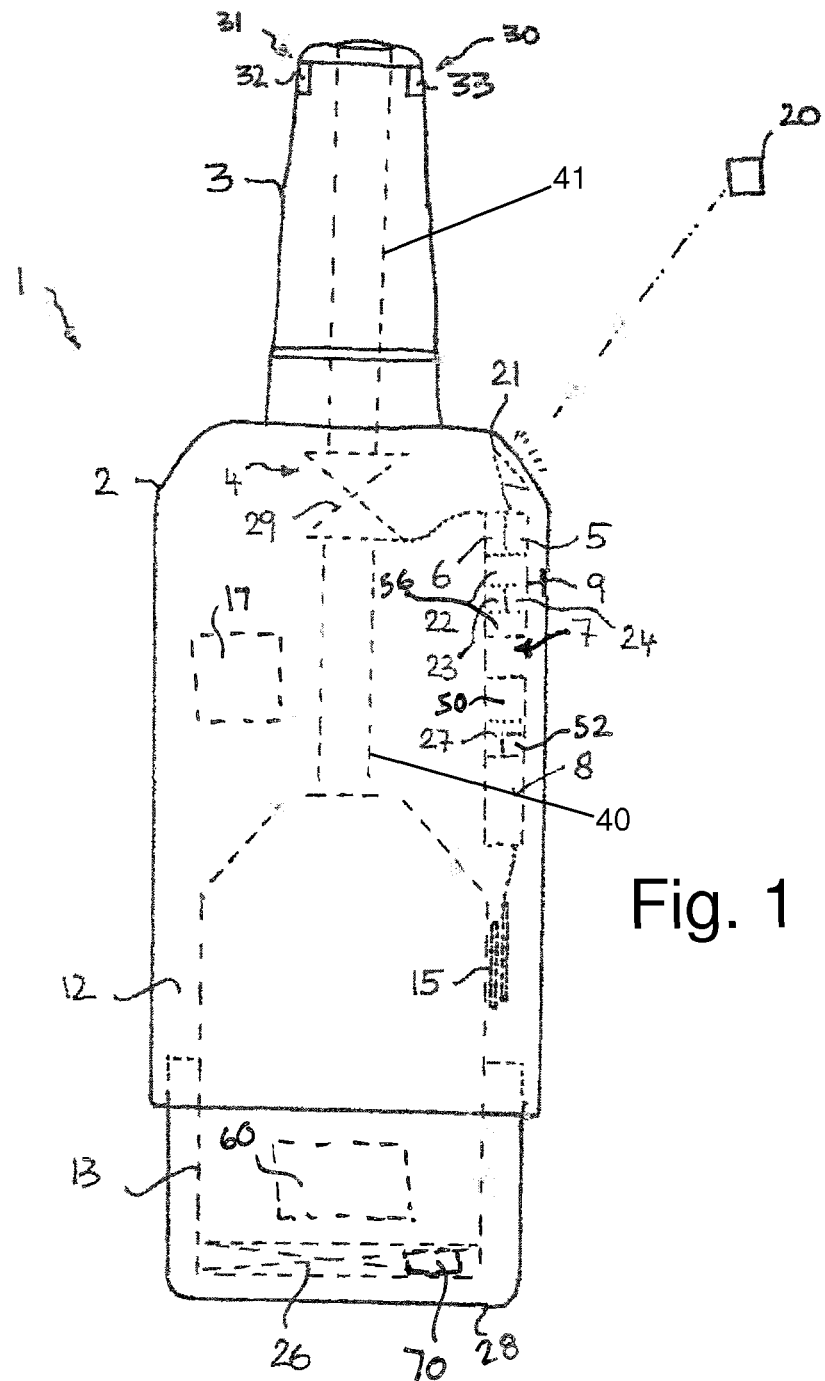
FIG. 1 shows a schematic representation of a nasal applicator according to an advantageous embodiment of the present disclosure.

As shown in FIG. 1, the nasal applicator 1 may include a basically cylindrical housing 2 on the top side of which a discharge mandrel 3 for insertion into a nostril protrudes. As used herein, the term "top" is used to refer to the side closer to the patient's nostril when the nasal applicator is in use, whereas the term "bottom" is used to refer to the side further from the patient's nostril when the nasal applicator is in use. In the depicted example, a top portion of housing 2 has a frustoconical shape with rounded edges. Discharge mandrel 3 may be formed as a conical section, as shown, with a chamfered top, to facilitate insertion into a patient's nostril. As shown, a diameter of the bottom of the discharge mandrel may be smaller than a diameter of the top of the frustoconical top portion of the housing.

The housing 2 may be adapted to have in its interior a mounting chamber or receiving chamber 12 and replaceably receive therein an active substance container 13 connectable to the dosage device 4 of the nasal applicator 1. Active substance container 13 may serve as a vessel for an active pharmaceutical substance 60, as schematically shown in FIG. 1. As shown, mounting chamber 12 may be shape-matched to the active substance container. For example, the active substance container may have a substantially cylindrical bottom portion and a substantially frustoconical top portion, and thus the mounting chamber may be shaped such that the frustoconical top portion of the active substance container and part of the cylindrical bottom of the active substance container fit closely therein. However, in other examples, the mounting chamber and active substance container may be shaped otherwise, and may or may not be shape-matched.

In order to replace the active substance container 13, the housing 2 may be opened for example by means of a cover 28, the active substance container 13 may be inserted and thereupon the cover 28 may be closed again. As shown, in one example, cover 28 may be formed as a hollow cylinder, with rounded edges at its bottom and a flat top. When cover 28 is in the closed position, its top portion may extend partially into the bottom of housing 2, as shown.

The transport of the active pharmaceutical substance from the inserted active substance container 13 is advantageously effected by means of an external energy-driven transport actuator 26 which may for example include a pressure gas cartridge or a spring device by means of which the active pharmaceutical substance 60 is expelled from the active substance container 13.

In order to dose the amount of active pharmaceutical substance, the said dosage device 4 includes, in accordance with FIG. 1, a dosage valve 29. As shown, dosage valve 29 may be arranged inside of housing 2 near a top portion of housing 2. In other examples, however, dosage valve 29 may be arranged elsewhere in the nasal applicator. Dosage device 4 may further include a tube 40 extending upward from the top of mounting chamber 12 to the bottom of dosage valve 29, and a tube 41 extending upward from the top of dosage valve 29 to the top of the nasal applicator. As shown, tube 41 may originate inside of housing 2 and extend through discharge mandrel 3, and may terminate slightly past the top of the nasal applicator. Mounting chamber 12 fluidly communicates with tube 40; depending on whether the dosage device is locked or unlocked (e.g., via dosage valve 29 as described below), mounting chamber 12 and tube 40 may also fluidly communicate with tube 41 such that the active pharmaceutical substance 60 may be delivered to a patient via tube 41.

Dosage valve 29 may be driven and actuated by an electronic control device 7, if for example a not shown mechanically-operated switch at the housing 2 is operated. The control device 7 may advantageously also be accommodated in the interior of the housing 2 and includes a patient data memory 8, from which the control device 7 may take control data individually predeterminable for a respective patient such as maximum dose, single dose or daily dose. Said control device 7 may for example be adapted to have a microcontroller and appropriate control modules such as for example a storage element or memory 50.

The control device 7 may lock said dosage device 4 by means of a locking device 6, for example if a maximum dose is reached or an unlocking code is not present. In order to detect and/or determine the actual discharged amount, the nasal applicator 1 includes dosage determination means such as dosage determining logic 5, which may for example be integrated into the control device 7 (e.g., stored in memory 50) and which may count the valve actuations of the dosage valve 29 and/or the length of the actuations.

Figure 3:
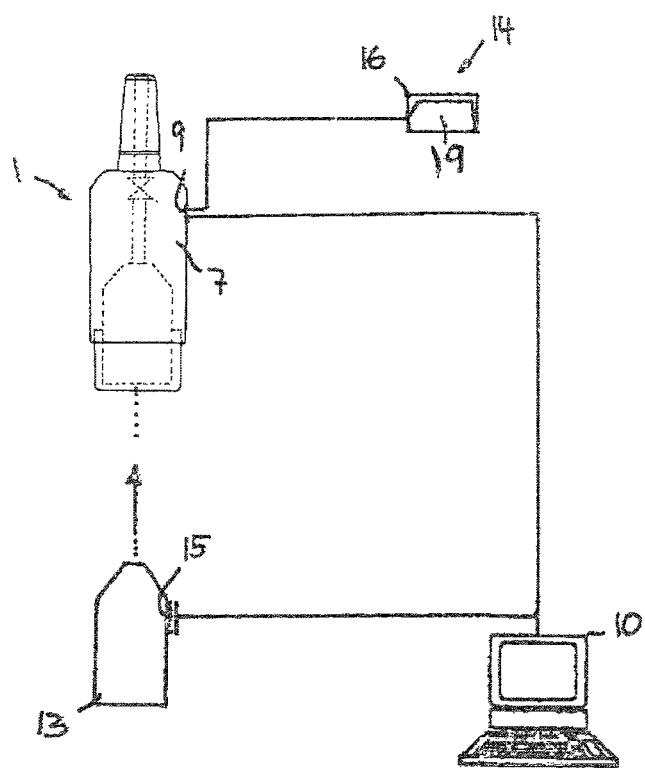
FIG. 3 shows a schematic representation of the programming options of the nasal applicator shown in FIG. 1.

The specific patient's individual control data may be made available to the control device 7 and/or the patient data memory 8 in a plurality of manners. As shown in FIG. 3, the control device 7 may be connected to an external computer 10 via a data communication interface 9, for example in the form of a USB interface, cf. FIG. 1, from which external computer 10 the control data may be programmed. Accordingly, in some examples, external computer 10 may be an input device which may enters individual control data for a specific patient into the control device and/or the patient data memory, for locking the dosage device for the patient as needed.

In the alternative or in addition, a memory chip 15 may be provided at the active substance container 13 insertable into the active substance container receiving chamber 12 of the housing 2, which memory chip 15 may be written on also from the external computer 10 via a suitable writing device. If the active substance container 13 is inserted into the nasal applicator 1, the control data stored on the chip element 15 are read out by the control device 7 via a suitable reader, cf. FIG. 1.

Alternatively or in addition, an input device 17 may be provided at the nasal applicator 1 itself in order to input a specific patient's individual control data. For example, as described above, input device 17 may be advantageously adapted such that it is sufficiently small to fit on the nasal applicator, e.g., in the form of a keyboard and/or small touch screen. While input device 17 is shown schematically in FIG. 1, it will be appreciated that input device 17 may be arranged at other locations on the exterior of housing 2 of the nasal applicator; for example, it may be arranged at a position which enables viewing of a keyboard and/or touch screen or other interface by the patient or by another user such as a medical professional assisting the patient.

In another example, an external input device 16 may be provided, the external input device 16 connectable for example via said interface 9, for example in the form of an input touch screen 19.

By way of input device 17 or external input device 16, e.g., said input touch screen 19, the patient is also given the opportunity to input at the device various discomfort data so as to provide a documentation of the level of discomfort, for example in the form of a numeric rating scale ranging from 0-10 according to which numeric values may be inputted or for example a scaling bar may be pulled and/or swept in a desired field ranging from "weak" to "strong". Said documentation of the level of discomfort may be stored simply for the purposes of documentation and be read out after the end of treatment and/or be used in order to modify the dosage algorithms. The modification of the dosage algorithms may in this connection be effected directly by the control logic of the device and/or by an external computer in dependency of the documented data.

Figure 2:
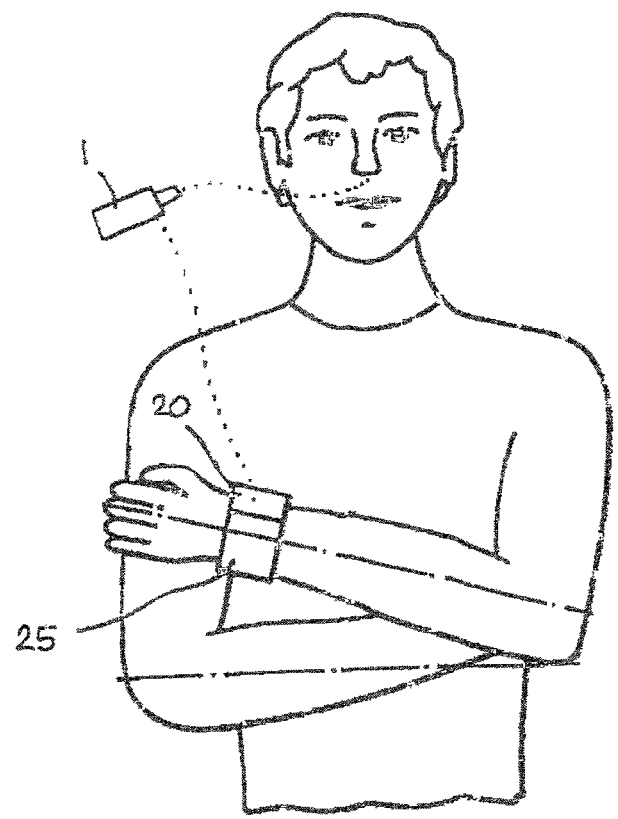
FIG. 2 shows a schematic representation illustrating the RFID control of the nasal applicator during use.

As is shown in FIG. 2, the nasal applicator 1 and/or the control device 7 thereof may further also communicate with an RFID element 20 which the patient wears on his body for example by means of a wristband or another body fastener 25. In such RFID element 20 a specific patient's individual control data, for example concerning the admissible maximum dose, and/or an unlocking code, which is the basis of activation of the nasal applicator 1 and/or unlocks the said locking device 6, may on the one hand be stored. For this purpose, the control device 7 may communicate by means of an RFID transmitter and/or receiver 21 with said RFID element 20, if the nasal applicator is positioned sufficiently close to the patient.

In an advantageous further development of the present disclosure the control data for locking in dependency of the administered and/or discharged active pharmaceutical substance may be stored directly in the nasal applicator 1, in particular the patient data storage 8 thereof and/or the chip 15 attached to the active substance container 13, whereas the specific user's individual unlocking code is stored in an external data memory, in particular in said RFID element 20.

In order to be able to determine whether active pharmaceutical substance discharged by the nasal applicator is in fact applied into the nose, the nasal applicator may include a determining device such as a position determining device 30, which may in a further development of the present disclosure be provided for example at or in the region of the discharge mandrel 3, in particular at the projecting end section thereof, which determining device determines the position of the discharge mandrel 3 in relation to the nose and/or the nasal cavity at the time of discharge of the active pharmaceutical substance. Said determining device 30 may in this connection be adapted to be heat-sensitive so as to determine the presence of body heat at the discharge mandrel 3, they may for example include a body temperature sensor 31 detecting normal body temperature, if such body temperature is present at the discharge mandrel 3.

The determining device 30 may in particular include at least one bi-metal element 32 and/or at least one infrared element 33 which may be positioned at the front side of the end section of the discharge mandrel 3, and which may in particular be incorporated into the nasal part in order to be able to detect thermal differences.

The determining device 30 may send their signal to the control device 7 which may then unlock the locking device 6 via unlocking logic 23, if the nasal part of the applicator is positioned inside the nose, and/or control the dosage determining logic 5 such that discharged amounts of active pharmaceutical substance 60 are only considered for determining the administered dose if the nasal part is located inside the nose. Unlocking logic 23 may comprise computer-readable instructions stored in memory 50 of control device 7, for example. To determine whether the nasal part of the applicator is positioned inside the nose, unlocking logic 23 may receive input data such as a signal from a user identification device 22. User identification device 22 may serve to automatically identify the user of the nasal applicator, for example by including a body feature sensor such as a fingerprint sensor. Alternatively, user identification device 23 may comprise a code receiver 24 for receiving a specific patient's individual code and comparing such received code with a predetermined code stored in memory of the control device (e.g., memory 50 or alternatively patient data memory 8). Accordingly, the nasal applicator may be unlocked by inputting and/or importing a code, whereas it may be locked when the correct code is not inputted and/or imported.

As noted above, in order to be able to easily configure and/or use the nasal applicator for a plurality of active pharmaceutical substances 60, in particular a plurality of painkillers, the control device may include a plurality of preconfiguration datasets 56 for preconfiguring the control of the locking device and/or the dosage device for a plurality of active pharmaceutical ingredients, from which preconfiguration datasets an appropriate preconfigured dataset is then selectable in dependency of a respective used active pharmaceutical substance. Such selection may be effected via the aforementioned input device, but also, as the case may be, by importing the respective preconfiguration data from the aforementioned external computer, wherein in such case the preconfiguration datasets are provided at the external computer.

In order to simplify the selection of the preconfiguration datasets 56, the control device of the nasal applicator may include an active pharmaceutical substance identification module 27 which automatically identifies the respective used active pharmaceutical substance and selects the appropriate preconfiguration data. To this purpose an appropriate, importable code may be attached to the active pharmaceutical substance container to be inserted, for example in the chip element 15 fixed to the active substance container or a bar code applied thereto. The active pharmaceutical substance identification module 27 at the nasal applicator includes suitable code detection means such as code detection logic 52, in order to import and/or detect the code provided at the active pharmaceutical substance container 13 and to select the correct preconfiguration data in dependency of the imported and/or detected code.

Advantageously, the described nasal applicator may in particular be used for administering highly effective opioid painkillers, wherein the nasal applicator may basically, however, also be used for discharging other medicaments or pharmaceuticals or pharmaceutical substances that are self-administered under the patient's control. In this connection, in particular substances are referred to that are sensibly administered under at least one of the following marginal conditions: (a) the disease and/or discomfort/symptoms to be treated occur suddenly and are not predicable in a sufficiently accurate manner (e.g. migraine attacks, nausea/vomiting, blood sugar fluctuations, epileptic fits, extreme blood pressure fluctuations); (b) the medicaments used for treatment of the abovementioned symptoms are quickly absorbed via the nasal mucous membrane and effect a quick alleviation of the discomfort; (c) the medicaments used for treatment of the symptoms mentioned under (a) bring about a certain risk potential or have strong side effects, e.g. they have to be applied within certain limits (for example so-called "triptanes" may be effective in a quick and reliable manner concerning migraine attacks, but may lead to a severely disturbed blood flow if overdosed); (d) the medicaments used for treatment of the symptoms mentioned under (a) may lead to dependency/addiction (example: opioids, anticonvulsants), so that in the context of a patient-controlled application the access has to be controlled and/or the patient has to be identified.

The described nasal applicator may further also advantageously be used for administering combinations of medicaments and/or active pharmaceutical substances, for example combinations of two different pharmaceuticals such as a pharmaceutical with different galenism, e.g., a quickly releasing painkiller in combination with a delayedly, i.e. retardedly releasing active substance portion. Such combinations of medicaments and/or active pharmaceutical substances may be stored in a joint active substance container 13 and may be administered therefrom. In the alternative thereto, the nasal applicator may, however, also be adapted such that two or more separate active substance containers 13 are insertable and/or attachable, so that the said medication combinations may be discharged via the applicator mandrel out of a plurality of active substance containers 13. The control device may in this connection be adapted such that both or a plurality of active pharmaceutical substances may be discharged simultaneously, or may also be adapted such that the active pharmaceutical substances are discharged one after the other, for example one substance at the first activation of the applicator and the other medicament at the second applicator activation.

The nasal applicator may have a modular structure and be composed of a plurality of applicator modules appropriate for an specific individual patient, wherein the applicator modules may comprise a nasal discharge mandrel 3, at least one active substance container 13 and a transport actuator 26 which are replaceably joinable and/or insertable into each other and/or mountable to a joint mounting plate, optionally in the form of a housing 2. In such an example, the transport actuator 26 may include a propellant 70 that is connectable to the active substance container 13 and contains an additive, such as an adjuvant, modifying the active pharmaceutical substance stored in the active substance container 13 so that by attaching different propellants 70 at least one property of the active pharmaceutical substance to be discharged from the active substance container 13 is variable to be adjusted to a specific individual patient by means of attaching different propellants.

Such a propellant offers the possibility of adding for example $CO_2$ in order to acidulate the medication mixture/aerosol and thereby increase the portion of lipophilic medicamentous fraction in pharmaceuticals which are present in aqueous solution as anionic bases and thus facilitate the diffusion of the medicament via the nasal mucous membrane.

The invention claimed is:

1. A nasal applicator for nasal administration of medicinal active pharmaceutical substances, comprising:
    a housing with a receiving chamber in its interior, an active substance container replaceably insertable into the receiving chamber, the active substance container serving as a vessel for an active pharmaceutical substance;
    a dosage device for dosedly discharging the active pharmaceutical substance, the dosage device comprising a transport actuator by means of which the active pharmaceutical substance is expelled from the active substance container, the transport actuator having the form of a pressure accumulator and/or spring accumulator driving a pump or piston acting on the active pharmaceutical substance stored in the active substance container;
    dosage determining logic for determining an amount of discharged active pharmaceutical substance; and
    a locking device for locking the dosage device when the determined amount of discharged active pharmaceutical substance reaches a predetermined level, wherein the locking device is controlled by an electronic control device including a patient data memory into which individual control data of a specific patient for individually locking the dosage device for the patient can be entered by an input device,
    wherein the control device includes a user identification device for automatically identifying a user of the nasal applicator and unlocking logic for unlocking the locking device in dependency of the respective determined user of the nasal applicator, the user identification device including a code receiver for receiving an individual code of the patient, wherein the user identification device compares the received code with a predetermined code.

2. The nasal applicator according to claim 1, wherein the locking device is activated when a maximum amount of the active pharmaceutical substance has been discharged, wherein the maximum amount of the active pharmaceutical substance is alterable by inputting of different control data into the patient data memory of the control device via the input device.

3. The nasal applicator according to claim 1, wherein the control device includes a data communication interface and wherein the input device comprises an external computer communicating with the control device via the data communication interface.

4. The nasal applicator according to claim 1, wherein the input device comprises a chip element, wherein the chip element is attachable to the active substance container, and wherein the chip element communicates with the control device and gives control commands to the nasal applicator upon insertion of the active substance container into the nasal applicator.

5. The nasal applicator according to claim 1, wherein the input device comprises a manually operable input device, the manually operable input device comprising:
    a communication menu including a display device for displaying input prompts and inputted input values and/or a touch screen; and
    an input element for inputting discomfort data;
    wherein the nasal applicator comprises a storage device for storing the inputted discomfort data; and
    wherein the control device comprises a control module for adjusting the patient's individual control data depending on the inputted discomfort data.

6. The nasal applicator according to claim 1, wherein the control device includes a wireless signal receiver for receiving the patient's individual control data.

7. The nasal applicator according to claim 6, wherein the wireless signal receiver is part of an RFID transmitter and/or receiver, and wherein the input device comprises an RFID element and the patient's individual control data are stored in the RFID element.

8. The nasal applicator according to claim 7, wherein the code receiver is formed by the RFID transmitter and/or receiver and the code is stored in the RFID element.

9. The nasal applicator according to claim 8, wherein the RFID element is fixed to a body fastener, the body fastener wearable by the patient.

10. The nasal applicator according to claim 7, wherein control data from the RFID element are transmittable only at a distance of less than a predetermined distance between the RFID element and the RFID transmitter and/or receiver.

11. The nasal applicator according to claim 1, wherein the control device comprises a plurality of pre-configured datasets for a plurality of active pharmaceutical substances for pre-configuring the control of the locking device and/or the dosage device, wherein an appropriate pre-configured dataset is selectable from such pre-configured datasets in dependency of the respective used active pharmaceutical substance, and wherein the control device further comprises an active pharmaceutical substance identification module for automatically identifying the respective used active pharmaceutical substance and automatically selecting the appropriate pre-configured dataset.

12. The nasal applicator according to claim 11, wherein the input device is fixed to the active substance container, and wherein the active pharmaceutical substance identification module comprises code detection logic for detecting a code applied to the active substance container.

13. The nasal applicator according to claim 1, wherein the dosage device comprises an electrically drivable dosing valve and the locking device is integrated into a drive module of the control device for driving the dosing valve.

14. The nasal applicator according to claim 1, wherein the nasal applicator has a modular structure including a nasal discharge mandrel which, together with the active substance container, is insertable into the nasal applicator.

15. The nasal applicator according to claim 1, wherein the transport actuator further comprises a propellant that is connectable to the active substance container and contains an adjuvant modifying the active pharmaceutical substance, wherein at least one property of the active pharmaceutical substance to be discharged from the active substance container may be varied for different patients by attaching different propellants.

16. The nasal applicator according to claim 1, wherein the active substance container has a substantially cylindrical bottom portion and a substantially frustoconical top portion.

17. The nasal applicator according to claim 16, wherein the receiving chamber is shape-matched to the active substance container such that the substantially frustoconical top portion of the active substance container and part of the cylindrical bottom of the active substance container fit closely in the receiving chamber.

18. A nasal applicator for nasal administration of medicinal active pharmaceutical substances, comprising:
    a housing with a receiving chamber in its interior, an active substance container replaceably insertable into the receiving chamber, the active substance container serving as a vessel for an active pharmaceutical substance;

a dosage device for dosedly discharging the active pharmaceutical substance, the dosage device comprising a transport actuator by means of which the active pharmaceutical substance is expelled from the active substance container, the transport actuator having the form of a pressure accumulator and/or spring accumulator driving a pump or piston acting on the active pharmaceutical substance stored in the active substance container;

dosage determining logic for determining an amount of discharged active pharmaceutical substance; and a locking device for locking the dosage device when the determined amount of discharged active pharmaceutical substance reaches a predetermined level, wherein the locking device is controlled by an electronic control device including a patient data memory into which individual control data of a specific patient for individually locking the dosage device for the patient can be entered by an input device, wherein a position determining device is provided for determining a position of the nasal applicator in/at a nose of the patient when discharging the active pharmaceutical substance from the nasal applicator, and wherein the control device further comprises unlocking logic for unlocking the locking device in dependency of the respective determined position of the nasal applicator in/at the nose, and wherein the position determining device comprises a heat detection device and/or a body temperature sensor for detecting a temperature adjacent to a nasal discharge mandrel which is insertable into the nasal applicator, and at least one bi-metal element and/or an infrared element at the nasal discharge mandrel.

19. The nasal applicator according to claim 18, wherein the dosage determining logic receives data from the position determining device and takes the data into account such that only an amount of active pharmaceutical substance discharged when the nasal applicator is positioned in and/or at the nose is determined as an administered dose.

* * * * *